US00PP26365P3

(12) United States Plant Patent
Austin

(10) Patent No.: US PP26,365 P3
(45) Date of Patent: Feb. 2, 2016

(54) SHRUB ROSE PLANT NAMED 'AUSLEVITY'

(50) Latin Name: *Rosa hybrida*
Varietal Denomination: AUSlevity

(71) Applicant: David Austin Roses Ltd., Albrighton, Wolverhampton (GB)

(72) Inventor: David J. C. Austin, Wolverhampton (GB)

(73) Assignee: DAVID AUSTIN ROSES LTD, Albrighton, Wolverhampton (GB)

( * ) Notice: Subject to any disclaimer, the term of this patent is extended or adjusted under 35 U.S.C. 154(b) by 98 days.

(21) Appl. No.: 13/999,981

(22) Filed: Apr. 11, 2014

(65) Prior Publication Data

US 2015/0296672 P1 Oct. 15, 2015

(51) Int. Cl.
*A01H 5/00* (2006.01)

(52) U.S. Cl.
USPC ..... Plt./104

(58) Field of Classification Search
USPC ..... Plt./101, 102, 104
See application file for complete search history.

*Primary Examiner* — Susan McCormick Ewoldt
(74) *Attorney, Agent, or Firm* — KPPB LLP

(57) ABSTRACT

A variety of rose plant of the shrub class, named 'AUSlevity'. The 'AUSlevity' is a variety of rose suitable for cut-flower production with large blooms containing frilly petals of rich buttery yellow paling to cream towards the edge, and demonstrating a strong, fragrance with hints of honey, lilac and almond.

1 Drawing Sheet

Classification: The present invention relates to a new *Rosa hybrida* shrub of the market class 'English Rose'.

Variety denomination: The new plant has the varietal denomination 'AUSlevity'.

ORIGIN OF INVENTION

This invention relates to a new and distinct variety of shrub rose plant named 'AUSlevity', which was originated from the cross-pollination of the two 'unnamed' and unpatented seedlings of *Rosa hybrida.*

BACKGROUND OF THE INVENTION

The primary objective of this breeding was to produce an English Rose variety suitable for cut-flower production with large blooms containing frilly petals of rich buttery yellow paling to cream towards the edge, and demonstrating a strong fragrance with hints of honey, lilac and almond.

SUMMARY OF THE INVENTION

Among the features which distinguish the new variety from others presently available and commercial rose cultivars known to the inventor is the following combination of characteristics: large blooms containing heavy frilled petals the color of a rich, buttery yellow that pales to cream toward the edge of the blooms, and demonstrating a strong fragrance with hints of honey, lilac and almond.

Asexual reproduction of the new variety by budding as performed at Bowling Green Lane in Albrighton, Britain shows that the foregoing and other distinguishing characteristics come true to form and are established and transmitted through succeeding asexual propagations. 'AUSlevity' may be asexually propagated by budding. The budding successfully occurred on the plant/rootstock *Rosa* 'Inermis' for the observed plants.

COMPARISON WITH PARENTS

The seed and pollen parents of 'AUSlevity' are two unnamed seedlings. The new rose may be distinguished from its seed parent, by the following combination of characteristics: the seed parent is a yellow hybrid tea bloom compared with the old-fashioned double bloom with frilly petals of 'AUSlevity'. The new rose may be distinguished from its pollen parent, by the following combination of characteristics: the parent is a pink rose compared with the yellow blooms of 'AUSlevity'.

COMPARISON WITH THE CLOSEST COMMERCIALLY AVAILABLE CULTIVAR

The closest commercially available cultivars to the new variety are the 'AUSjameson' (U.S. Plant Pat. No. 17,159). The new rose may be distinguished from the 'AUSjameson' variety by the following combination of characteristics: the 'AUSjameson' has petals that are rounder with edges that are mostly entire, whereas the petals of 'AUSlevity' are obovate with frilly edges. In addition, in 'AUSjameson' the color of the quarter-blown buds are orange (RHS 28C), whereas in 'AUSlevity' the buds are yellow (RHS 12A), and when the blooms are fully open 'AUSjameson' is more apricot, whereas 'AUSlevity' is more yellow and fades to cream toward its outer edges.

BRIEF DESCRIPTION OF ILLUSTRATION

The accompanying photograph illustrates the new variety and shows the flowering thereof from bud to full bloom depicted in color as nearly correct as it is possible to make in a color illustration of the character.

Throughout this specification, color references and/or values are based upon The Colour Chart of The Royal Horticultural Society (2001) except where common terms of color definition are employed.

DESCRIPTION OF THE NEW VARIETY

Observations of budded 'AUSlevity' specimens were made at the nursery at David Austin Roses Limited in Albrighton, Wolverhampton, United Kingdom. The following description is of 6 year-old potted rose plants of the new variety grown indoors in a greenhouse in Albrighton, Britain in the month of June. Phenotypic expression may vary with environmental, cultural and climatic conditions, as well as differences in conditions of light and soil.

Flower characteristics:

*Blooming habit.*—Continuous. The number of blooms per plant during the growing season is profuse, but there are too many to count.

*Bud.*—Size: About 2 cm long and 1.9 cm in diameter when the petals start to unfurl. Form: The bud form is pointed ovoid and broad based. Color: When sepals first divide, the bud color is RHS 151C (yellow-green group). When half blown, the upper sides of the petals are RHS 12A (yellow group), and the lower sides of the petals are RHS 12A (yellow group). Calyx: Shape: star-shaped when the bloom is open, folding back against the stem. Length: 7 cm. Diameter: 7 cm. Sepals: Arrangement: Regular. Color: Upper Surface: green RHS 147C (yellow-green group). Lower Surface: green RHS 144A (yellow-green group). Length: 3 cm. Width: 1.2 cm. Shape: Lanceolate. Surface texture: Upper Surface: Downy. Lower Surface: Slightly downy. Number: There are 2 lightly appendaged sepals, and 3 unappendaged sepals with hairy edges. Receptacles: Color: RHS 143C (yellow-green group). Shape: funnel. Size: broad, about 1 cm high×0.8 cm wide. Surface: Smooth. Peduncle: Length: medium, averaging about 8 cm. Surface: Smooth. Color: RHS 143C (green group) with RHS 181A (greyed-red group). Strength: Normal.

*Blooms.*—Size: Large, average open diameter is about 10 cm. Borne: Mostly singly. (Note: the inflorescence when the shrub is growing naturally may hold between 1 and 6 blooms, and then has a rounded shape. When grown commercially for cut-flower production the stems are disbudded to ensure the blooms are grown singly.) Stems: Strength: Normal, average length is about 40 cm. Diameter: 4 mm. Form: When first open, bloom is cupped. Permanence of bloom: outer petals curl back.

*Petalage.*—Number of petals under normal conditions: 83. Color: The upper sides of the petals are mostly RHS 9C (yellow group), with the outer edge of the petal being a paler RHS 27D (orange group). The reverse sides of the petals are mostly RHS 10B (yellow group), with the outer edge being a very pale pink RHS 36B (red group). The base of the outer petals has no yellow spot, as the major yellow color of the petal reaches down to the base. Variegations: None. Discoloration: The general tonality at the end of the first day is RHS 9B (yellow group), and at the end of the third day is RHS 10C (yellow group). With further aging the color then further changes to RHS 158C (yellow-white group). Fragrance: Strong. Character of fragrance: fruity with hints of honey, lilac and almond.

*Petals.*—Texture: Leathery. Size: Width: 5 cm. Length: 5 cm. Surface: Smooth. Shape: Obovate. Margin: Strong undulation of margin, with weak reflexing. Apex Shape: Heavily frilled, some that are notched. Base Shape: Obtuse. Form: Incurved with frilled edges. Arrangement: Quartered. Petaloids: Number: about 3. Color: RHS 20A (yellow-orange group). Length: 7 mm. Width: 4 mm. Shape: Elliptic. Margin: Irregular. Persistence: Petals hang on and dry. Lastingness: On the plant: not tested. As a cut flower: About 10 days.

*Reproductive parts.*—Stamens: Number: 140. Length: 5-9 mm. Anthers: Length: 3 mm. Color: RHS 21C (yellow-orange group). Arrangement: Regular around styles. Filaments: Color: RHS 21C (yellow-orange group). Length: 3-6 mm. Pollen: Color: RHS 21A (yellow-orange group). Pistils: Number: 70. Length: 15 mm. Styles: Color: RHS 145D (yellow-green group). Length: 13 mm. Stigmas: Color: RHS 7A (yellow group). Length: 2 mm. Hips: None Observed.

Plant characteristics:

*Plant form.*—Shrub, English Rose.

*Plant growth.*—Medium.

*Age to maturity.*—One year.

*Mature plant.*—Height: 75 cm. Width: 75 cm.

*Rootstock.*—*Rosa* 'Inermis' for the observed plants.

*Foliage.*—Number: Leaflets on normal mid-stem leaves is: 5. Size: Medium, about 15 cm long×13 cm wide. Quantity: Abundant. Number of leaves per flowering stem is: 10. Color: New foliage: Upper side: RHS 146B (yellow-green group) tinged with RHS 181A (greyed-red group). Lower side: RHS 146C (yellow-green group) overlaid with some RHS 181A (greyed-red group). Old foliage: Upper side: RHS 137A (green group). Lower side: RHS 137C (green group).

*Leaflets.*—Size: About 8 cm long×5 cm wide. Shape: Pointed oval. Base Shape: Obtuse. Apex Shape: Acuminate. Texture: Leathery. Edge: Serrated. Serrations: Single. Petiole: Color: RHS 143A (green group) with RHS 181A (greyed-red group). Length: 3 cm. Width: 1.8 m. Surface Texture: Rough, glandular. Petiole Rachis: Color: RHS 143A (green group) with RHS 181A (greyed-red group). Underside: with occasional prickles and slightly glandular. Stipules: Length: 2.5 cm, glandular. Color: RHS 143C (green group). Auricle: Shape: Lanceolate. Length: 7 mm. Width: 2 mm. Color: RHS 143C (green group). Vein Color: Same as leaf color. Venation Pattern: Reticulate.

*Wood.*—New Wood: Color: RHS 143C (green group) with RHS 181A (greyed-red group). Bark: Smooth. Old Wood: Color: RHS 143C (green group) with RHS 181A (greyed-red group). Bark: Smooth.

*Branching habit.*—Number: None.

*Stems.*—Mature Stem: Length: 63 cm. Diameter: 6 mm. Internode Distance: 4 cm. The above measurements are all variable, depending on growing conditions in a season. Stem Pubescence Present: No.

*Prickles.*—Quantity: On main canes from base: Few. Number per stem length: 10 per 10 cm. Form: Deep concave. Length: 5 mm. Color when young: RHS181B (greyed-red group). Color when mature: RHS 199D (greyed-brown group).

*Small prickles.*—Quantity: Main stalk: None.

*Disease resistance.*—Mildew: Resistant. Blackspot: Not tested. Rust: Not tested.

*Pest resistance.*—Not tested.

*Winter hardiness.*—Not tested.

*Growing conditions.*—Normal greenhouse conditions.

What is claimed is:

1. A new and distinct variety of rose plant of the shrub class suitable for cut flower production, substantially as herein shown and described.

* * * * *

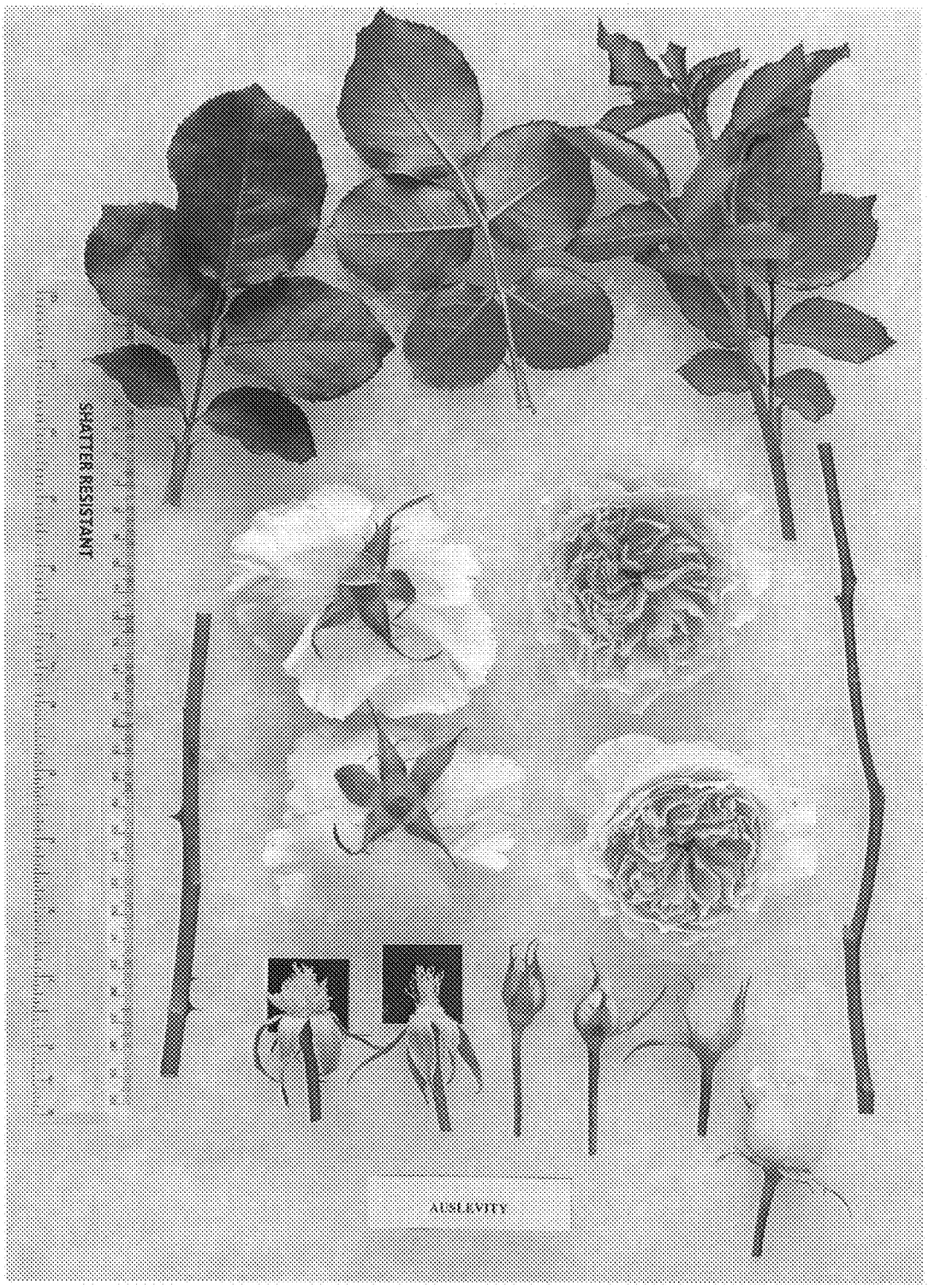
AUSLEVITY
SHATTER RESISTANT